United States Patent [19]

Bromidge et al.

[11] Patent Number: 5,773,619

[45] Date of Patent: Jun. 30, 1998

[54] PROCESS FOR THE PREPARATION OF AZABICYCLOC DERIVATIVES

[75] Inventors: Steven Mark Bromidge, Sawbridgeworth; Martyn Voyle, Welwyn; Erol Ali Faruk, Enfield; Mark Jason Hughes, Welwyn; John Kitteringham, Hertford; Gary Thomas Borrett, Stansted, all of England

[73] Assignee: SmithKline Beecham p.l.c., Brentford, England

[21] Appl. No.: 439,616

[22] Filed: May 12, 1995

[30] Foreign Application Priority Data

May 14, 1994 [GB] United Kingdom .................... 9409705

[51] Int. Cl.$^6$ ................................................ C07D 453/02
[52] U.S. Cl. ........................................................ 546/133
[58] Field of Search .................................. 546/112, 133; 540/477, 585, 1

[56] References Cited

U.S. PATENT DOCUMENTS

| 3,857,848 | 12/1974 | Mauvernay et al. . |
| 3,904,632 | 9/1975 | Hollander ................................ 260/285 |
| 4,598,093 | 7/1986 | Tahara .................................... 514/538 |
| 5,418,240 | 5/1995 | Sauerberg et al. . |

FOREIGN PATENT DOCUMENTS

| 1014958 | 8/1977 | Canada . |
| 0 392 803 | 10/1990 | European Pat. Off. ...... C07D 453/02 |
| 2323303 | 12/1973 | Germany . |
| WO 92/03433 | 3/1992 | WIPO .......................... C07D 453/02 |
| WO 93/17018 | 9/1993 | WIPO .......................... C07D 453/02 |
| WO9317018 | 9/1993 | WIPO . |

OTHER PUBLICATIONS

Sandler, et al., "Organic Functional Group Preparations", Academic Press, vol. III, pp. 367–381 (1972).
Zh. Obshch. Khim, 32 2935 (1962).
Mar., J. Advanced Organic Chemistry, Wiley, 1992, pp. 592–593.
Philllips, R.R., Org. React. 1959, pp. 143–178.

*Primary Examiner*—C. Warren Ivy
*Assistant Examiner*—Garth M. Dahlen
*Attorney, Agent, or Firm*—Linda E. Hall; Stephen A. Venetianer; Edward T. Lentz

[57] ABSTRACT

A process for the preparation of a compound of formula (I) or a pharmaceutically acceptable salt thereof:

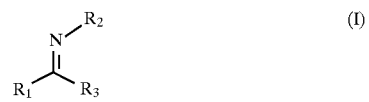

wherein $R_1$ represents

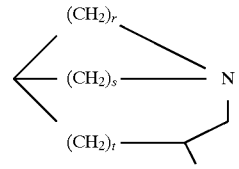

in which r represents an integer of 2 to 4, s represents 1 or 2 and t represents 0 or 1;

$R_2$ is a group $OR_4$, where $R_4$ is $C_{1-4}$ alkyl, $C_{2-4}$ alkenyl or $C_{2-4}$ alkynyl or a group $OCOR_5$ where $R_5$ is hydrogen or $R_4$; and $R_3$ is CN;

said process comprising reacting a compound of formula (II):

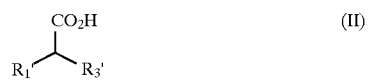

wherein $R_1'$ is $R_1$ or a group convertible thereto, and $R_3'$ is an electron withdrawing group, with a source of nitrous acid, and thereafter converting the resulting =NOH group to =$NR_2$ wherein $R_2$ is as defined in formula (I), converting $R_1'$ and $R_3'$ when other than $R_1$ and $R_3$ to $R_1$ and $R_3$, and thereafter optionally forming a pharmaceutically acceptable salt.

22 Claims, No Drawings

PROCESS FOR THE PREPARATION OF AZABICYCLOC DERIVATIVES

This invention relates to a process for the preparation of compounds having pharmaceutical activity.

EP-A-0392803 (Beecham Group p.l.c.) discloses certain azabicyclic compounds which enhance acetylcholine function via an action at muscarinic receptors within the central nervous system.

These compounds are therefore of potential use in the treatment and/or prophylaxis of dementia in mammals. Various preparative methods are also disclosed.

WO93/17018 and WO 92/03433 disclose certain routes to intermediates useful in the preparation of certain compounds disclosed in EP-A-0392803.

We have now developed an improved process for the preparation of one class of the compounds disclosed in EP-A-0392803.

The present invention provides a process for the preparation of a compound of formula (I) or a pharmaceutically acceptable salt thereof:

wherein
$R_1$ represents

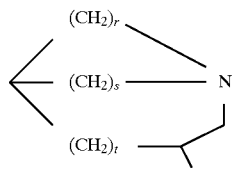

r represents an integer of 2 to 4, s represents 1 or 2 and t represents 0 or 1;
$R_2$ is a group $OR_4$, where $R_4$ is $C_{1-4}$ alkyl, $C_{2-4}$ alkenyl or $C_{2-4}$ alkynyl or a group $OCOR_5$ where $R_5$ is hydrogen or $R_4$; and
$R_3$ is CN;
said process comprising reacting a compound of formula (II):

wherein $R_1'$ is $R_1$ or a group convertible thereto, and $R_3'$ is an electron withdrawing group, with a source of nitrous acid and thereafter converting the resulting =NOH group to =$NR_2$ wherein $R_2$ is as defined in formula (I), converting $R_1'$ and $R_3'$ when other than $R_1$ and $R_3$ to $R_1$ and $R_3$, and thereafter optionally forming a pharmaceutically acceptable salt.

Compounds of formula (I) are capable of existing in a number of stereoisomeric forms including geometric isomers such as E and Z and, for certain compounds, enantiomers. The different stereoisomeric forms may be separated one from the other by the usual methods.

If desired, the compounds of formula (I) can be formed into acid addition salts with acids, such as the conventional pharmaceutically acceptable acids, for example hydrochloric, hydrobromic, phosphoric, acetic, fumaric, salicylic, citric, lactic, mandelic, tartaric, oxalic and methanesulphonic.

The term pharmaceutically acceptable salt encompasses solvates and hydrates. Thus where compounds of formula (I) or pharmaceutically acceptable salts thereof form solvates or hydrates, these also form an aspect of the invention.

Preferred combinations of (r,s,t) include (2,2,0), (2,1,1), (3,1,1), (2,1,0) and (3,1,0), most preferably (2,2,0).

The groups $R_4$ and $R_5$ in $R_2$ are preferably selected from methyl, ethyl, allyl and propargyl. Suitable values for $R_2$ include methoxy, ethoxy, allyloxy, propargyloxy and acetoxy, preferably methoxy.

Examples of suitable electron withdrawing groups include CN, $CO_2R$ and $CON(R)_2$ in which each R is independently H, $C_{1-8}$ alkyl, $C_{2-8}$ alkenyl, $C_{2-8}$ alkynyl, $C_{3-8}$ cycloalkyl, $C_{3-8}$ cycloalkyl $C_{1-4}$ alkyl or aryl $C_{1-4}$ alkyl, wherein aryl groups are selected from optionally substituted phenyl and naphthyl. Suitable examples of substituents on phenyl and naphthyl include one or more, for example 1 to 3, substituents selected from halo, hydroxy, $C_{1-4}$ alkoxy and $C_{1-4}$ alkyl. $R_3'$ is preferably CN.

The compound of formula (II) may be provided in the form of an ester hydrolysed to the free acid prior to reaction with the source of nitrous acid.

The reaction of the compound of formula (II) with the source of nitrous acid, for example an alkali metal nitrite such as sodium nitrite may be carried out in aqueous acid such as hydrochloric acid for example at 0° C. to 50° C.

After basification, the reaction results in a compound of formula (III):

When $R_1'$ is $R_1$ where (r, s, t) is (2, 2, 0) and $R_3'$ is CN, the Z isomer of the compound of formula (III) may be crystallised out from the reaction mixture in the zwitterionic form. Compounds of formula (III) in zwitterionic form are novel and as such form part of the invention.

The =NOH group of the oxime of formula (III) may be converted to =$NR_2$ by conventional routes, for example compounds where $R_2$ is $OCOR_5$ can be made by acylation with an acylating agent such as an acyl halide, for example acetyl chloride. Compounds where $R_2$ is $OR_4$ can be made by alkylation with an alkylating agent such as methyl tosylate (methyl p-toluene sulphonate) or an alkyl halide, for example methyl iodide. The alkylation is preferably carried out at a temperature of −20° C.–40° C., more preferably 0° C.–40° C., for example 18° C.–36° C., most preferably below 35° C., and is preferably preceded by treatment of oxime of formula (III) with base such as potassium t-butoxide.

$R_3'$ groups other than CN may be converted thereto conventionally, for example by conversion, if necessary, to the primary amide followed by dehydration.

Examples of $R_1'$ groups other than $R_1$ include suitable azacyclic precursors which may be cyclised as described in, for example, EP 0392803.

The different stereoisomeric forms of compounds of formula (I) may be separated one from the other by the usual methods, for example chromatographic methods or during treatment of the compound of formula (I) or earlier intermediates such as of formula (III) with chiral resolving agents. Enantiomers may be separated using chiral resolving agents such as L-(+)-tartaric acid, D-(+)-malic acid, gulonic acid derivatives such as 2,3:4,6-di-O-isopropylidene-2-keto-L-gulonic acid, camphorsulphonic acid, dibenzoyl tartaric acid, mandelic acid and (S)-(+)- and (R)-(−)-1,1'-binaphthyl-2,2'-diyl hydrogen phosphate, or chiral chromatography. For resolution of the compound of formula (I), where (r, s, t) is (2, 2, 0), $R_2$ is methoxy and $R_3$ is CN, 2,3:4,6-di-O-isopropylidene-2-keto-L-gulonic acid is particularly preferred and can achieve separation of the E/Z geometric isomers. The resolution process forms a further aspect of the invention. The unwanted enantiomer obtained from the separation may be racemised by treatment with a strong base such as potassium t-butoxide and the resulting mixture of enantiomers and geometric isomers separated again to furnish the required isomer. For resolution of the compound of formula (III) where $R_1'$ is $R_1$, (r,s,t) is (2,2,0) and $R_3'$ is CN, L-(+)-tartaric and D-(+)-malic acids are particularly preferred and the resolution process forms a further aspect of the invention.

Accordingly, the invention therefore provides a process for resolving [R,S]-α-(methoximino)-α-(1-azabicyclo[2.2.2]oct-3-yl)acetonitrile, optionally obtained by the process of the invention, which comprises treating the racemic compound with 2,3:4,6-di-O-isopropylidene-2-keto-L-gulonic acid, separating the resolved R-(Z) isomer as the crystalline gulonate salt, optionally racemising the mother liquors with strong base and obtaining a further crop of resolved R-(Z) isomer gulonate salt by repeating the treatment process, and thereafter converting the resolved R-(Z) isomer into the free base or a pharmaceutically acceptable salt.

The invention further provides a process for resolving racemic [R,S-(Z)]-α-(oximino)-α-(1-azabicyclo[2.2.2]oct-3-yl)acetonitrile which comprises treating the racemic compound, optionally obtained by the process of the invention, with L-(+)-tartaric or D-(+)-malic acid, separating the resolved R-(Z) isomer as the crystalline tartrate or malate salt and thereafter converting the salt to the free base.

In the preparation of the desired R-(Z) isomer of the compound of formula (I), where (r,s,t) is (2,2,0), $R_2$ is methoxy and $R_3$ is CN, it is preferred to obtain the Z isomer of the intermediate compound of formula (III) as described above. The Z isomer of the oxime of formula (III) may be resolved into the desired R enantiomer before methylation of the =NOH group. It has been found that base treatment of the resolved oxime does not result in unwanted racemisation of the oxime and that methylation proceeds smoothly to the required R-(Z) isomer of the final compound. This methylation process forms another aspect of the invention.

The invention therefore provides a process for preparing [R-(Z)]-α-(methoxyimino)-α-(1-azabicyclo[2.2.2]oct-3-yl) acetonitrile or a pharmaceutically acceptable salt thereof which comprises treating [R-(Z)]-α-(oximino)-α-(1-azabicyclo[2.2.2]oct-3-yl)acetonitrile, optionally obtained by the resolution process of the invention, with base, methylating the product and thereafter optionally forming a pharmaceutically acceptable salt.

Methylation may result in some alkylation on the oxime nitrogen to give a nitrone. Hydrolysis of the reaction mixture after methylation with aqueous base such as $K_2CO_3$ at elevated temperature for example 50°–60° C. results in removal of the nitrone side product.

Higher enantiomeric purity can be achieved, if required, by recrystallisation of the chiral salt from a suitable solvent such as water (for compounds of formula (III)) or ethyl acetate/methanol (for compounds of formula (I)).

The invention also provides a process for preparing a compound of formula (III) which process comprises reacting a compound of formula (II) with a source of nitrous acid such as an alkali metal nitrite and thereafter converting $R_1'$ and $R_3'$ when other than $R_1$ and $R_3$ to $R_1$ and $R_3$ and thereafter optionally forming a salt.

Compounds of formula (II) can be prepared from corresponding compounds of formula (IV) or esters thereof:

by hydrogenation according to standard procedures optionally followed by ester hydrolysis and conversion of $R_1'$ and $R_3'$ to $R_1$ or CN respectively.

The reduction of compounds of formula (IV) and their esters is preferably carried out by treating a solution of a compound of formula (IV) or ester with hydrogen under atmospheric or elevated pressure, in the presence of a precious metal catalyst such as Palladium on carbon. The resulting compound of formula (II) may be isolated or alternatively the reaction product may be used directly in the reaction with the source of nitrous acid.

Compounds of formulae (II) and (IV) are novel and as such form part of the invention.

Compounds of formula (IV) may be prepared by reacting a compound of formula (V):

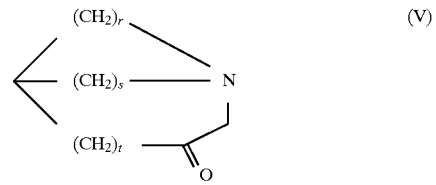

with a compound $R_3'$ $CH_2CO_2H$ or the ester, optionally followed by conversion of $R_1'$ and/or $R_3'$ to $R_1$ or CN respectively.

The reaction of a compound of formula (V) may be carried out in aqueous base, such as sodium hydroxide at moderate temperatures, for example ambient to 50° C.

Where the $R_3'$ group is a carboxy derivative such as an alkoxycarbonyl group, it may be converted to a cyano group by conventional methods as described above, but preferably before hydrogenation or the reaction with alkali metal nitrite.

However, as stated above, $R_3'$ is preferably cyano and no conversion is necessary.

Intermediates of formula (V) are known compounds (e.g. as described in Thill et al., J. Org. Chem., 1968, 33, 4376) or may be prepared analogously.

The compounds of formula (I) are useful in therapy as described in EP-0392803.

The following Examples illustrate the invention.

EXAMPLE 1

Preparation of [R,S-(Z)]-α-(oximino)-α-(1-azabicyclo[2.2.2]oct-3-yl)acetonitrile Method A Stage 1 Preparation of 1-azabicyclo[2.2.2]oct-3-ylidenecyanoacetic Acid A mixture of quinuclidinone hydrochloride (32 g, 0.2 mol) and cyanoacetic acid (20.2 g, 1.2 eq) in water (65 ml) was mechanically stirred until a solution resulted. This was then cooled to approx 10° C. by immersion in an ice-water bath and sodium hydroxide pellets (27.0 g, 3.4 eq) added portionwise with stirring over 1 h while maintaining the reaction temperature at 15°–25° C. with the aid of the ice-bath. The resulting solution was then stirred at approx. 20° C. for an additional 1.5 h after which time a thick suspension of the sodium salt of the product was deposited and the temperature of the mixture rose to 25° C.

Stirring was continued for another 1 h at room temperature before adding dropwise conc HCl (37 ml) over 0.5 h while maintaining the temperature of the mixture at approx. 20° C. with external cooling. As the acid was added the suspension dissolved to give a near-solution before the free acid of the product was deposited during the latter stages of the addition. The final pH of the mixture was fine-adjusted to pH7 after which stirring was continued for another 0.5 h and the mixture then left to stand at room temperature for 48 h. It was then re-stirred while chilling to 0°–5° C. for 3 h before filtering under suction. The filter cake was washed with a little ice-cold water and then dried, first under suction and then under high vacuum at 40°–45° C. overnight. Yield: 34.0 g (90%).

NMR (250 MHz, $D_2O$) δ=2.02–2.17 (2H, m), 2.19–2.34 (2H, m), 3.30–3.57 (5H, m), 4.61 (2H, s).

Stage 2 Preparation of α-cyano-1-azabicyclo[2.2.2]octane-3-acetic Acid

The Stage 1 nitrile acid (20 g, 0.1 mol) was suspended in water (100 ml) and 5% Pd—C paste (type 87L, 61% moisture, 3.0 g) added. The mixture was stirred vigorously under hydrogen at atmospheric pressure for 22 h. It was then filtered through celite under suction to give a solution of the reduced nitrile acid, the identity and purity of which was checked by NMR ($D_2O$) of an evaporated aliquot. The solution of Stage 2 product was used directly for the next stage.

NMR (250 MHz, $D_2O$) δ=1.85–2.24 (4.35H, m), 2.30–2.36 (0.65H, m), 2.63–2.80 (1H, m), 3.08–3.45 (5H, m) 3.56–3.77 (1H, m).

Stage 3 Preparation of Title Compound

The Stage 2 solution was chilled with stirring to 0°–5° C. using an ice bath during which conc. HCl (19 ml, 0.24 mol) was also added over 1–2 min. A solution of $NaNO_2$ (17 g, 0.25 mol) in water (230 ml) was then added dropwise over 1 h while maintaining the temperature at 0°–5° C. An initial very pale blue solution formed which turned greenish, while evolution of gas ($CO_2$) also became quite apparent. After the addition was complete the mixture was left to stir in the ice-bath while allowing to warm slowly to room temperature overnight. An NMR ($D_2O$) of the residue from a basified and evaporated aliquot showed an E:Z mixture (approx. 1:4 ratio) of the oxime to be present. The neutral reaction mixture was stirred and basified to pH8–9 by dropwise addition of a solution of NaOH (4.17 g, 0.1 mol) in water (6 ml), over 10 min during which the zwitterionic Z-isomer of the product precipitated out. The suspension was stirred while chilling to 0°–5° C. for three hours, after which it was left to stand at this temperature overnight before filtering under suction. The filter cake was washed with a little ice-cold water before drying under suction and then under high vacuum at 40°–45° C. to afford the Example 1 title compound. Yield: 12.6 g (68%).

NMR (250 MHz, $D_2O$) δ=1.82–2.15 (4H, m), 2.36–2.44 (1H, m), 3.20–3.43 (5H, m), 3.50–3.65 (1H, m), 3.67–3.78 (1H, m).

The mother liquor from the filtration was acidified with conc. HCl (20 ml) and then left to stand at room temperature for 18 h to convert the predominantly E-isomer present into Z-isomer. Basification to pH 8–9 with 40% aq. NaOH yielded a second crop of title compound which was similarly filtered off and dried. Yield: 2.2 g (12%).

Method B

Stage 1 Preparation of 1-azabicyclo[2.2.2]oct-3-ylidenecyanoacetic Acid

40% Aqueous NaOH (370 ml, 3.7 mol) was added to a stirred suspension of 3-quinuclidinone hydrochloride (600 g, 3.7 mol) in water (300 ml) over 30 min while maintaining the temperature at 15°–25° C. The resulting mixture was then cooled to 15° C. and a solution of cyanoacetic acid (380 g, 4.5 mol) in water (150 ml) added in a steady stream over 30 min while stirring and maintaining the temperature at 15°–20° C. After the addition was complete, further 40% aq. NaOH (900 ml, 9.0 mol) was added gradually over 45 min while stirring and maintaining the temperature at 15°–20° C. The resulting reddish solution was then left to stir at ambient temperature for a further 2 h before cooling to 15° C. Seeding with authentic sodium 1-azabicyclo[2.2.2]oct-3-ylidenecyanoacetate induced crystallisation of the same, and the mixture was then chilled further to 7° C. with stirring until a thick slurry of the sodium salt was obtained. After stirring at this temperature for a further 45 min a mixture of conc HCl (725 ml) and water (725 ml) was added in a steady stream over 45 min while stirring and maintaining the temperature at 15°–20° C. After adjusting to pH7 the resulting slurry of the Stage 1 product was stirred at ambient temperature for an additional 45 min before using directly for Stage 2.

Stage 2 Preparation of α-cyano-1-azabicyclo[2.2.2]octane-3-acetic Acid

10% Pd—C catalyst (type 487, dry powder, 66 g) was added to the slurry of the Stage 1 product and the mixture then stirred under hydrogen at atmospheric pressure for 65 h. It was then filtered through celite under suction to give a solution of the Stage 2 product, the identity and purity of which was checked by NMR ($D_2O$) of an evaporated aliquot. The solution was used directly for the next stage.

Stage 3 Preparation of Title Compound

The Stage 2 solution was chilled with stirring to 7° C. and conc HCl (790 ml, 9.3 mol) added over 5 min. The stirred mixture was chilled back to 4° C. before adding a solution of $NaNO_2$ (360 g, 5.2 mol) in water (510 ml+60 ml washings) over 1 h while maintaining the temperature at 4°–6° C. An initial very pale blue solution formed which turned greenish, while evolution of gas ($CO_2$) also became quite apparent. After the addition was complete the mixture was left to stir at 4°–6° C. for an additional 2 h before allowing to warm slowly to room temperature overnight. An NMR ($D_2O$) of the residue from a neutralised and evaporated aliquot showed an E:Z mixture (~1:5) of the oxime to be present together with a little unreacted 3-quinuclidinone (3–4%).

The reaction mixture was stirred and 40% aq. NaOH (390 ml, 3.9 mol) added in a steady stream over 1 h while maintaining the temperature at 20°–25° C. During the addition the zwitterionic Z-oxime product precipitated out. The addition of the 40% aq. NaOH was continued until a final pH of 8–9 was obtained. The resulting suspension of Z-oxime was then chilled to 4°–5° C. with stirring and maintained at this temperature for 2 h before filtering under suction. The filter cake was washed with ice-cold water (600 ml) before leaving to suck dry overnight. The product was finally dried to constant weight at 50°–55° C. under high vacuum to afford the title compound. Yield: 455 g (68% from 3-quinuclidinone hydrochloride).

EXAMPLE 2

Preparation of [R-(Z)]-α-(oximino)-α-(1-azabicyclo[2.2.2]oct-3-yl)acetonitrile

Stage 1

To a stirred suspension of racemic zwitterionic [R,S-(Z)]-α-(oximino)-α-(1-azabicyclo[2.2.2]oct-3-yl) acetonitrile from Example 1 (20.0 g, 0.11 mol) in water (148 ml) at 35° C. was added a solution of L(+) tartaric acid (16.8 g, 0.11 mol) in water (100 ml) at 30° C. The resultant mixture was warmed to 50° C., giving a homogenous solution which was then stirred at ambient temperature for 20 h. The crystalline product was filtered off, washed with water (20 ml) then sucked dry on the filter.

Stage 2

The damp solid from Stage 1 was slurried with water (49 ml) and heated to 95° C., giving a homogenous solution. This solution was stirred at ambient temperature, and seed crystals of authentic [R-(Z)]-α-(oximino)-α-(1-azabicyclo[2.2.2]oct-3-yl)acetonitrile L-(+)-tartrate salt were added at intervals until crystallisation occurred. Stirring was continued at ambient temperature for 16 h. The crystalline product was filtered off, washed with water (8 ml) then sucked dry to give the tartrate salt in high enantiomeric purity (e.e.>99%), (2.5 g, 68%).

NMR (250 MHz, DMSO) δ=1.65 (2H, m), 1.85 (2H, m), 2.22 (1H, m), 2.95–3.20 (5H, m), 3.35 (2H, d, J=7Hz), 4.05 (2H, s).

Stage 3

A slurry of [R-(Z)]-α-(oximino)-α-(1-azabicyclo[2.2.2]oct-3-yl)acetonitrile L-(+)-tartrate salt from Stage 2 (12.5 g, 38 mmol) in water (60 ml) was stirred and heated to 95° C., giving a homogenous solution. Aqueous sodium hydroxide (10M) was added to this solution in 0.5 ml portions. A graph of solution pH v volume of base added was plotted, and the end point for base addition was determined as the second rapid pH change. A total of 7.5 ml of base was added. The mixture was cooled to 0° C., then stirred at this temperature for 1.5 h. The crystalline solid was filtered off, washed with a small volume of cold water, then dried in vacuo at 60° C. to give the title compound (6.3 g, 93%) of high enantiomeric purity (e.e.>99.8%).

NMR (400 MHz, DMSO) δ=1.38 (1H, m), 1.48 (1H, m), 1.60 (2H, m), 2.00 (1H, m), 2.65–2.75 (5H, m), 2.90–3.05 (2H, m), 13.10 (1H, s, br).

EXAMPLE 3

Preparation of [R,S-(Z)]-α-(methoxyimino)-α-(1-azabicyclo[2.2.2]oct-3-yl)acetonitrile Zwitterionic [R,S-(Z)]-α-(oximino)-α-(1-azabicyclo[2.2.2]oct-3-yl)acetonitrile from Example 1 (35.1 g, 196 mmol) was suspended in a mixture of DMSO (250 ml) and THF (175 ml) and stirred under nitrogen while cooling to 10° C. Potassium tert-butoxide (21.9 g, 195 mmol) was added in one lot and stirring continued for approx. 0.5 h until a yellow solution resulted. The temperature rose to reach 15° C. before dropping back with external cooling. The temperature of the solution was brought down to −1° C. using an acetone/CO₂ bath before a solution of methyl tosylate (36.0 g, 194 mmol) in THF (75 ml) was added dropwise over 45 min while maintaining the reaction temperature at 0°–2° C. The mixture was stirred for an additional 0.5 h at 0°–5° C. by which time a thick yellow suspension had formed. Ice-cold water (100 ml) was added and the resulting solution transferred to a separating funnel containing further water (100 ml). The mixture was extracted with EtOAc (200 ml+5×130 ml portions) and the combined extracts washed with water (3×40 ml) and then brine (20 ml+40 ml) before drying over Na₂SO₄. Evaporation afforded the title compound as a mobile yellow oil, 91% pure by HPLC relative assay. Yield: 29.4 g (78%).

NMR (250 MHz, CDCl₃) δ=1.40–1.55 (1H, m), 1.58–1.80 (3H, m), 2.07–2.20 (1H, m), 2.60–3.14 (6H, m), 3.20–3.34 (1H, m), 4.08 (3H, s).

EXAMPLE 4

Preparation of [R-(Z)]-α-(methoxyimino)-α-(1-azabicyclo[2.2.2]oct-3-yl)acetonitrile Method A Resolution of [R,S-(Z)]-α-(methoxyimino)-α-(1-azabicyclo[2.2.2]oct-3-yl)acetonitrile To a solution of [R,S-(Z)]-α-(methoxyimino)-α-(1-azabicyclo[2.2.2]oct-3-yl)acetonitrile from Example 3 (105.3 mg, 0.55 mmol) in ethanol (0.1 ml) was added a solution of 2,3:4,6-di-O-isopropylidene-2-keto-L-gulonic acid monohydrate (79.7 mg, 0.27 mmol) in ethanol (0.5 ml). The resultant solution was stirred at ambient temperature, then allowed to stand for 16 h. The crystalline product was filtered off, washed with a small volume of cold ethanol then dried in vacuo at 60° C. to give the title compound as its 2,3:4,6-di-O-isopropylidene 2-keto-L-gulonate salt, (44.5 mg, 34%) in high enantiomeric purity (e.e.>97%).

NMR (250 MHz, DMSO) δ=1.20 (3H, s), 1.32 (3H, s), 1.38 (3H, s), 1.40 (3H, s), 1.60 (2H, m), 1.78 (2H, m), 2.16 (1H, m), 2.75–3.15 (5H, m), 3.20 (2H, m), 3.85 (1H, m), 3.95–4.10 (2H, m), 4.05 (3H, s), 4.20 (1H, m), 4.66 (1H, s).

Method B

Resolution of E/Z mixture of [R,S]-α-(methoxyimino)-α-(1-azabicyclo[2.2.2]oct-3-yl)acetonitrile Stage I A solution of [R,S-(E,Z)]-α-(methoxyimino)-α-(1-azabicyclo[2.2.2]oct-3-yl)acetonitrile (41 g) was dissolved in ethyl acetate (100 ml) and a solution of 2,3:4,6-di-O-isopropylidene-2-keto-L-gulonic acid monohydrate (22.5 g, 0.077 mol) in ethyl acetate (400 ml) was added. Crystallisation occurred whilst standing for 16 hours. The crystals were isolated by filtration to give the 2,3:4,6-di-O-isopropylidene-2-keto-L-gulonate salt (19.3 g, 0.041 mol, 54%).

Stage 2

A solution of [R,S-(E,Z)]-α-(methoxyimino)-α-(1-azabicyclo[2.2.2]oct-3-yl)acetonitrile in ethyl acetate (the mother liquors from the crystallisation in Stage 1), was washed with 5% aqueous potassium carbonate solution, then washed with saturated aqueous potassium carbonate solution and concentrated. The residue was dissolved in THF (ca 30 wt % solution), and potassium tert-butoxide (5 wt %) was added. After 1 hour the reaction was partitioned between ethyl acetate and 5% aqueous potassium carbonate solution. The organic phase was separated, washed (5% aq K₂CO₃), dried, filtered through silica and concentrated to give a racemic mixture.

The racemic mixture was used as a starting material for a resolution in accordance with Stage 1.

EXAMPLE 5

Preparation of [R-(Z)]-α-(methoxyimino)-α-(1-azabicyclo[2.2.2]oct-3-yl)acetonitrile Monohydrochloride Method A Stage 1—Isolation of Title Compound as Free Base The salt from Example 4, Method B, Stage 1 (86 g) was dissolved in water (400 ml) and the solution made basic with saturated aqueous potassium carbonate. The solution was extracted with ethyl acetate (500 ml) and the extract washed with 5% aqueous potassium carbonate (2×100 ml) then saturated aqueous potassium carbonate (2×20 ml). The combined aqueous phases were extracted with a further 400 ml of ethyl acetate and the extract washed as above. The combined ethyl acetate extracts were dried over potassium carbonate and concentrated to give the free base (38 g).

Stage 2—Salt Formation (Title Compound)

The free base from Stage 1 (63 g; 0.33 mol) was dissolved in isopropyl alcohol (500 ml) and concentrated hydrochloric acid (28 ml, 0.33 mol) was added. The mixture was diluted with ethyl acetate (11) and the solid collected by filtration, washed with ethyl acetate (2×100 ml) and dried at ambient temperature under reduced pressure (1 mm Hg) for 4 hours to give the title compound (43.9 g).

A second crop was obtained by concentrating the mother liquor to ~250 ml and adding ethyl acetate (500 ml). This was washed and dried as above (14.3 g).

Method B

Zwitterionic [R-(Z)]-α-(oximino)-α-(1-azabicyclo[2.2.2]oct-3-yl)acetonitrile from Example 2 (6.0 g, 34 mmol) was suspended in a mixture of DMSO (42 ml) and THF (12 ml) and stirred under nitrogen whilst cooling to 7° C. Potassium tert-butoxide (3.76 g, 33 mmol) was added in one portion. The cooling bath was removed and stirring was continued for 15 min during which time a homogenous solution formed and the temperature rose to 13° C. This solution was cooled to 7° C., then a solution of methyl tosylate (6.84 g, 37 mmol) in THF (6 ml) was added dropwise whilst maintaining the reaction mixture temperature at ≦13° C. The resultant mixture was stirred at ambient temperature for 2 h, then aqueous potassium carbonate (0.2M, 30 ml) was added in one portion. The temperature rose to ca. 40° C., then was further raised to 55°–60° C. and maintained at this temperature for 2 h. The resultant solution was extracted with ethyl acetate (3×30 ml), and the combined extracts were washed with aqueous potassium carbonate (0.2M, 18 ml) and water (18 ml). Propan-2-ol (100 ml) was added and the solution evaporated to a volume of 10–20 ml. Additional propan-2-ol (60 ml) was then added and the solution again evaporated to a volume of 10–20 ml. The volume was increased to 27 ml by the addition of propan-2-ol and the solution cooled to 5° C. Concentrated hydrochloric acid (2.0 ml, 24 mmol) was added slowly with stirring, keeping the temperature below 12° C. This mixture was stirred for 15 min, then ethyl acetate (60 ml) was added portionwise. The mixture was stored at 4° C. for 16 h, then the crystalline solid was filtered off, washed with a small volume of ethyl acetate then dried in vacuo at 30° C. to give the title compound (3.1 g, 40%).

NMR (250 MHz, DMSO) δ=1.75 (2H, m), 1.95 (2H, m), 2.33 (1H, m), 3.05–3.28 (4H, m), 3.28–3.55 (3H, m), 4.08 (3H, s), 11.12 (1H, s, br).

Abbreviations
DMSO dimethyl sulphoxide
THF tetrahydrofuran
EtOAc ethyl acetate

We claim:

1. A process for the preparation of a compound of formula (I) or a pharmaceutically acceptable salt thereof:

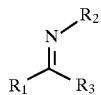

wherein $R_1$ represents

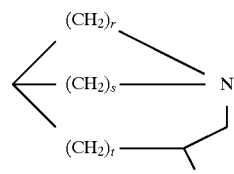

in which r repzesents 2, s represents 2 and t represents 0;

$R_2$ is a group $OR_4$, where $R_4$ is $C_{1-4}$ alkyl, $C_{2-4}$ alkenyl or $C_{2-4}$ alkynyl or a group $OCOR_5$ where $R_5$ is hydrogen or $R_4$; and $R_3$ is CN;

said process comprising reacting a compound of formula (II):

wherein $R_1$l is $R_1$, and $R_3'$ is CN, with a source of nitrous acid, and thereafter converting the resulting =NOH group to =$NR_2$ wherein $R_2$ is as defined in formula (I), converting $R_1'$ and $R_3'$ when other than $R_1$ and $R_3$ to $R_1$ and $R_3$, and thereafter optionally forming a pharmaceutically acceptable salt.

2. A process according to claim 1 wherein $R_2$ is methoxy.

3. A process according to claim 1 wherein the source of nitrous acid is an alkali metal nitrite.

4. A process according to claim 3 wherein the nitrite is sodium nitrite.

5. A process according to claim 1 wherein different stereoisomeric forms of the compound of formula (I) are separated one from the other.

6. A process according to claim 5, wherein the optical isomers are resolved by treatment with 2,3:4,6-di-O-isopropylidene-2-keto-L-gulonic acid.

7. A process for preparing a compound of formula (III):

wherein $R_1'$ and $R_3'$ are as defined in claim 1, which process comprises reacting a compound of formula (II):

wherein $R_1'$ and $R_3'$ are as defined for formula (III), with a source of nitrous acid, and thereafter optionally forming a salt.

8. A process according to claim 7 wherein the source of nitrous acid is sodium nitrite.

9. A compound of formula (II)

wherein $R_1'$ represents

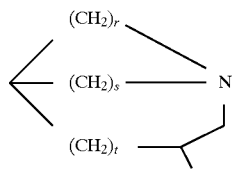

in which r represents 2, and s represents 2 and t represents 0, and $R_3'$ is CN.

10. A compound of formula (IV)

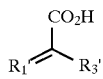 (IV)

wherein $R_1'$ represents

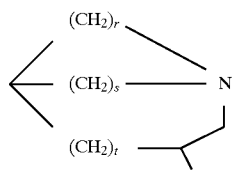

in which r represents 2, and s represents 2 and t represents 0, and $R_3'$ is CN.

11. A process for resolving [R,S]-α-(methoximino)-α-(1-azabicyclo[2.2.2]oct-3-yl)acetonitrile which comprises treating the racemic compound, optionally prepared according to claim 1, with 2,3:4,6-di-O-isopropylidene-2-keto-L-gulonic acid, separating the resolved R-(Z) isomer as the crystalline gulonate salt, optionally racemising the mother liquors with strong base and obtaining a further crop of resolved R-(Z) isomer gulonate salt by repeating the treatment process, and thereafter converting the resolved R-(Z) isomer into the free base or a pharmaceutically acceptable salt.

12. A process for resolving [R,S-(Z)]-α-(oximino)-α-(1-azabicyclo[2.2.2]oct-3-yl)acetonitrile which comprises treating the racemic compound, optionally prepared according claim 7, with L-(+)-tartaric or D-(+)-malic acid, separating the resolved R-(Z) isomer as the crystalline tartrate or malate salt and thereafter converting the salt to the free base.

13. A process for preparing [R,-(Z)]-α-(methoxyimino)-α-(1-azabicyclo[2.2.2]oct-3-yl)acetonitrile or a pharmaceutically acceptable salt thereof which comprises treating [R-(Z)]-α-(oximino)-α-(1-azabicyclo[2.2.2]oct-3-yl)acetonitrile, prepared according to claim 12, with base, methylating the product and thereafter optionally forming a pharmaceutically acceptable salt.

14. A process according to claim 1 for preparing [R-(Z)]-α-(methoxyimino)-α-(1-azabicyclo[2.2.2]oct-3-yl)acetonitrile.

15. A process according to claim 1 for preparing [R-(Z)]-α-(methoxyimino)-α-(1-azabicyclo[2.2.2]oct-3-yl)acetonitrile monohydrochloride.

16. A process for preparing [R-(Z)] α-(methoxyimino)-α-(1-azabicyclo[2.2.2]oct-3-yl)acetonitrile or a pharmaceutically acceptable salt thereof which comprises treating [R-(Z)]-α-(oximino)-α-(1-azabicyclo[2.2.2.]oct-3-yl)acetonitrile, prepared according to claim 7, with base, methylating the product and thereafter optionally forming a pharmaceutically acceptable salt.

17. A process according to claim 6, for preparing [R-(Z)]-α-(methoxyimino)-α-(1-azabicyclo[2.2.2.]oct-3-yl)acetonitrile.

18. A process according to claim 6, for preparing [R-(Z)]-α-(methoxyimino)-α-(1-azabicyclo[2.2.2.]oct-3-yl)acetonitrile monohydrochloride.

19. A process according to claim 11, for preparing [R-(Z)]-α-(methoxyimino)-α-(1-azabicyclo[2.2.2.]oct-3-yl)acetonitrile.

20. A process according to claim 11, for preparing [R-(Z)]-α-(methoxyimino)-α-(1-azabicyclo[2.2.2.]oct-3-yl)acetonitrile monohydrochloride.

21. A process according to claim 13, for preparing [R-(Z)]-α-(methoxyimino)-α-(1-azabicyclo[2.2.2.]oct-3-yl)acetonitrile monohydrochloride.

22. A process according to claim 13 for preparing [R-(Z)]-α-(methoxyimino)-α-(1-azabicyclo[2.2.2.]oct-3-yl)acetonitrile.

* * * * *